United States Patent
Melrose et al.

(10) Patent No.: US 10,226,482 B2
(45) Date of Patent: Mar. 12, 2019

(54) COPOLYMER AND METHOD FOR TREATMENT OF BACTERIAL INFECTION

(71) Applicant: RECCE LIMITED, Bentley, Western Australia (AU)

(72) Inventors: Graham John Hamilton Melrose, Mount Claremont (AU); Michele Keryn Dilizia, Hillarys (AU)

(73) Assignee: RECCE PHARMACEUTICALS LIMITED, Bentley, Western Australia (AU)

( * ) Notice: Subject to any disclaimer, the term of this patent is extended or adjusted under 35 U.S.C. 154(b) by 0 days.

(21) Appl. No.: 15/508,737

(22) PCT Filed: Nov. 17, 2015

(86) PCT No.: PCT/AU2015/050721
§ 371 (c)(1),
(2) Date: Mar. 3, 2017

(87) PCT Pub. No.: WO2016/077879
PCT Pub. Date: May 26, 2016

(65) Prior Publication Data
US 2017/0281669 A1    Oct. 5, 2017

(30) Foreign Application Priority Data

Nov. 18, 2014 (AU) .................... 2014904635
Nov. 25, 2014 (AU) .................... 2014904763
Jul. 3, 2015 (AU) .................... 2015902630

(51) Int. Cl.
| | | |
|---|---|---|
| A61K 31/78 | (2006.01) |
| A61K 31/77 | (2006.01) |
| A61P 31/04 | (2006.01) |
| C08F 16/34 | (2006.01) |
| A61K 9/00 | (2006.01) |
| C08G 65/26 | (2006.01) |

(52) U.S. Cl.
CPC ............ *A61K 31/77* (2013.01); *A61K 9/0053* (2013.01); *A61K 31/78* (2013.01); *A61P 31/04* (2018.01); *C08F 16/34* (2013.01); *C08G 65/2603* (2013.01); *C08G 2650/38* (2013.01); *C08G 2650/58* (2013.01); *Y02A 50/473* (2018.01)

(58) Field of Classification Search
None
See application file for complete search history.

(56) References Cited

U.S. PATENT DOCUMENTS 6,060,571 A    5/2000    Werle et al.

FOREIGN PATENT DOCUMENTS

| WO | 03061672 A1 | 7/2003 |
| WO | 2005044874 A1 | 5/2005 |
| WO | 2009059350 A1 | 5/2009 |

OTHER PUBLICATIONS

Rappé et al., Annual Review of Microbiology, 2003, vol. 57, pp. 369-394. (Year: 2003).*
International Search Report for corresponding application PCT/AU2015/050721 dated Feb. 15, 2016.
Written Opinion of the International Searching Authority for corresponding application PCT/AU2015/050721 dated Feb. 15, 2016.
International Preliminary Report on Patentability for corresponding application PCT/AU2015/050721 dated Oct. 6, 2016.

* cited by examiner

*Primary Examiner* — Savitha M Rao
*Assistant Examiner* — Gregg Polansky
(74) *Attorney, Agent, or Firm* — Norris McLaughlin PA (57) ABSTRACT

A method of treatment of infection in a subject comprising administering to the subject a copolymer comprising an acrolein derived segment or a polyacrolein oligomer segment and a polyalkylene glycol oligomer segment, the copolymer having a molecular weight of no more than 1500 Daltons.

23 Claims, 4 Drawing Sheets

COPOLYMER AND METHOD FOR TREATMENT OF BACTERIAL INFECTION

The present application is filed as a 35 USC 371 application of PCT/AU2015/050721 filed 17 Nov. 2015, which in turn claims the priority benefit of AU 2014904635 filed 18 Nov. 2014; AU 2014904763 filed 25 Nov. 2014; and, AU 2015902630 filed 3 Jul. 2015. The present application claims the full priority benefit to all of the foregoing applications and incorporates the entirety of their disclosures as if set forth herein.

FIELD

The invention relates to a method of treatment of bacterial infection, particularly parenteral bacterial infection, using a copolymer comprising an acrolein derived segment and a polyalkylene glycol oligomer segment wherein the copolymer has a molecular weight of up to 1500 Daltons, preferably up to 1000 Daltons, and to a process for the preparation of the copolymer by polymerization of acrolein in an aqueous solution of the polyalkylene glycol.

BACKGROUND

Parenteral infections (as distinct from infections of the gastrointestinal tract) occur when an organism gets access to inter-cellular and intra-cellular components underneath the outer-protective membranes or the skin. Punctures, injections, bites, cuts, wounds, surgery, splits between skin and mucous membranes are all examples which lead to parenteral infection. Parenteral infection does not include infections within the lumen of the gastro-intestinal tract.

Parenteral infections, particularly bacterial infection via a parenteral route, can lead to serious and life threatening disease with inflammatory response. If not controlled, parenteral infection can lead to sepsis with loss of blood-pressure, putting a subject at risk of a life threatening level of infection.

The most common origins that develop into sepsis are infections of the blood (bacteremia), meninges, lungs, urinary tract, sinuses, skin, wounds, abscesses and surgical procedures. Studies of common causative organisms associated with sepsis show that about 53% of cases are associated with gram-positive bacteria and about 42% with gram-negative bacteria.

Examples of gram-negative bacteria implicated in the development of sepsis include *Proteus* spp, *Serratia* spp, *Pseudomonas aeruginosa, Neisseria meningitidis, Escherichia coli, Klebsiella pneumoniae*. Examples of gram-positives implicated include *Staphylococcus aureus*, coagulase-negative *Staphylococcus* spp, *Streptococcus pyogenes, Streptococcus pneumoniae, Enterococcus* spp.

Routinely, sepsis and/or inter-related bacteremia are treated either preventatively (prophylactively) and/or curatively by antibiotics; a well-recognised statistic is that probability of life-survival recedes 6% for each hour-delay in treatment. However, identifying the bacteria at the root of the problem can take days—and even then the antibiotics used don't always work. Antibiotic resistance is leading to further increases in the risk of sepsis and this risk is often exacerbated in hospitals where antibiotic resistance can be particularly high due to the prevalence of the use of antibiotics.

About 30% of the people diagnosed with sepsis die, which makes it one of the leading causes of death in the intensive care unit of most hospitals. It kills approximately 120,000-200,000 people annually in the United States. World-wide, 13 million people develop sepsis each year, and as many as 4 million people die as a result.

The increasing threat of antibiotic-resistant bacteria to the world's population is recognized universally.

The threat is more critical when the infection is caused by an antibiotic-resistant bacterium ("super-bug"). There is an urgent need for the antibiotic which will allow treatment of a wide range of bacterial parenteral infections so as to provide greater certainty of immediate effective treatment of parenteral bacterial infections including bacteria which have become resistant to one or more of the antibiotics currently used.

Acrolein is extremely damaging to body tissues due to its high reactivity. Pure polyacrolein, alone is not known to exhibit significant antimicrobial activity. However, a number of patents (Melrose et al. 1988; Melrose 1996; Melrose and Huxham 2000; Melrose et al. 2001; Staton and Melrose 2002; Melrose et al. 2003; Tilbrook 2005; Melrose 2009) disclose the preparation and uses of modified polyacroleins as antimicrobial agents in the gastrointestinal tract. Acrolein is an extremely reactive monomer and when polymerized, rapidly forms a high molecular weight intractable network. Normally, anionic polymerizations are conducted in a solvent free of water and provide rapid polymerizations to form high molecular weight polymers.

The prior art ascribes the antimicrobial activity of the modified polyacroleins to their chemically reactive carbonyl groups, which in the gastrointestinal tract, are stated to destructively react with protein of microbes' outer membranes. One of the perceived advantages of the polymers described in the prior art is that they cannot penetrate the gut wall so that their activity is confined to the gastrointestinal tract. Melrose 2009 describes a polyacrolein polymer which may be formed by base catalyzed polymerization of acrolein and/or its acetal with an alkanol. The polymers have the advantage of a reduced propensity to migrate through membranes.

U.S. Pat. No. 6,060,571 (Werle et al.) describes acrolein releasing polymers which release sufficient acrolein to provide activity as sanitizing agents in water systems. Such polymers are not suitable for use in vivo due to the toxicity of the significant levels of acrolein released in aqueous media.

We have now found that low molecular weight copolymers comprising an acrolein derived segment and polyalkylene glycol oligomer segment may be prepared so as to limit the molecular weight of the copolymer to no more than 1500 Daltons, preferably no more than 1000 Daltons. Further we have found that the low molecular weight copolymers provide potent antimicrobial activity for treatment of parenteral infections, without release of acrolein monomer. Indeed the activity has been found to be enhanced when compared with acrolein polymers of higher molecular weight.

The discussion of the background to the invention herein is included to explain the context of the invention. This is not to be taken as an admission that any of the material referred to was published, known or part of the common general knowledge as at the priority date of any of the claims.

SUMMARY

Accordingly we provided a method of treatment of a parenteral infection in a subject comprising administering to the subject a copolymer comprising an acrolein derived segment and a polyalkylene glycol oligomer segment (preferably of molecular weight of from 200 to 600 Daltons), the copolymer having a molecular weight of no more than 1500 Daltons, preferably no more than 1000 Daltons.

In one set of embodiments we provided a method of treatment of a parenteral infection in a subject comprising administering to the subject a copolymer comprising a polyacrolein oligomer segment and a polyalkylene glycol oligomer segment (preferably of molecular weight of from 200 to 600 Daltons), the copolymer having a molecular weight of no more than 1500 Daltons, preferably no more than 1000 Daltons.

There is also provided use of a copolymer comprising an acrolein derived segment such as a polyacrolein oligomer segment and a polyalkylene glycol oligomer segment (preferably of molecular weight in the range of from 200 to 600 Daltons), in manufacture of a medicament for treatment of a parenteral infection in a subject wherein the copolymer is for oral or parenteral administration to the subject, the copolymer having a molecular weight of no more than 1500 Daltons, preferably no more than 1000 Daltons.

In one set of embodiments the acrolein derived segment is a polyacrolein oligomer.

In a further aspect there is provided a copolymer comprising an acrolein derived segment and a polyalkylene glycol oligomer segment (preferably of molecular weight from 200 to 600 Daltons), the copolymer having a molecular weight of no more than 1500 Daltons, preferably no more than 1000 Daltons. The copolymer is generally for treatment of a parenteral infection in a subject—either a prophylactic or a curative treatment.

The acrolein derived segment in one set of embodiments is a polyacrolein oligomer.

In yet a further aspect there is provided a process for preparation of a copolymer comprising an acrolein derived segment (such as a polyacrolein oligomer) and a polyalkylene glycol oligomer comprising copolymerizing acrolein and polyalkylene glycol oligomer under conditions of alkaline catalysis of pH no more than 12.0 and within a pH range of 12.0 to 7.0.0 in an aqueous solution comprising at least 20% w/w water, and the polyalkylene glycol oligomer (preferably of molecular weight of from 200 to 600 Daltons) in a weight ratio of polyalkylene glycol/acrolein of at least 4, preferably at least 10.

Definitions

The term "body" means the body of humans and/or animals; the term "subject" means such a body which is the subject.

Intravenous therapy (IV therapy or iv therapy in short) is the infusion of liquid substances directly into a vein.

As used herein, the term "parenteral" means taken into the body in a manner other than through the intact digestive canal. That is, not within the normal stomach or intestine; not intestinal.

The term "parenteral infection" refers to infection contracted by being taken into the body not within the gastrointestinal tract. Such infection may occur via the vascular (blood/lymph) system, the genital-urinary tracts, from the lungs, disruption of the skin or outer-protective membranes such as in surgery, needle stick injuries, cuts, abrasions, or any break in the skin or gaps between the skin and mucous membranes. It will be understood that a clear distinction is to be made between parenteral infection which may potentially be treated via any method of drug administration including oral administration (assuming an effective dose reaches the site of infection)—and parenteral administration of a drug which is limited to administration other than orally.

As used herein when referring to a bacterial pathogen, the term "antibiotic-resistant" or "superbug" refers to a bacterial pathogen that is capable of withstanding an effect of an antibiotic used in the art to treat the bacterial pathogen (i.e., a non-resistant strain of the bacterial pathogen). For example, Staphylococcus aureus can be treated using methicillin; however, an antibiotic-resistant strain of Staphylococcus aureus, S. aureus USA300, is a methicillin-resistant Staphylococcus aureus (MRSA). Although the bacterial strain is common, S. aureus: USA:300 typically infects those who are immunocompromised or in a susceptible environment. Infections will often enter the body through a small cut or sore. Other symptoms associated with USA:300 are pneumonia, necrotizing fasciitis, endocarditis, and bone and joint infection.

The term "pulmonary administration" refers to administration of a formulation of the invention into the lungs by inhalation.

The term "systemic" refers to a disease or disorder or original site of injury distant to the original site of infection, or involving the entire body of the organism. The term "local" therefore is used herein with respect to the site of original infection. Thus, a systemic infection is one in which the pathogen is found in the organs or blood (including bacteremia), and may be associated with a serious, potentially life threatening disease such as sepsis. A local infection is one in which the pathogen has migrated only as far as the local tissue of infection such as the lung or site of a wound.

As used herein, the term "inhalation" refers to intake of air to the alveoli of the lung. In specific examples, intake can occur by self-administration of a formulation of the invention while inhaling, or by administration via a respirator, e.g., to a patient on a respirator. The term "inhalation" used with respect to a formulation of the invention is synonymous with "pulmonary administration."

The terms "treatment" and "treating" are intended to encompass also prophylaxis, therapy and cure. Accordingly, in one aspect, a treatment involves preventing or delaying or slowing the onset of a condition, disease, or disorder (e.g. the symptoms associated with the disease, condition, or disorder) associated with antibiotic resistant bacteria. In another aspect, a treatment involves treating (e.g. minimizing or reducing or slowing the development or reversing) an existing condition, disease, or disorder (e.g. the symptoms associated with the disease, condition, or disorder) associated with antibiotic resistant bacteria. In one embodiment, a treatment provides a cure for a condition, disease, or disorder.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject copolymer and/or composition from one organ, or portion of the body, to another organ, or portion of the body. Each carrier must be "acceptable" in the sense of being compatible with the other ingredients of the formulation and not unduly injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The copolymer may be used in a therapeutically-effective (or "pharmaceutically-effective or active") amount to provide treatment of the parenteral infection. The amount will depend on the mode of administration such as oral, intramuscular, intravenous, inhalation or transdermal administration. The phrase "therapeutically-effective amount" as used herein means that amount of a copolymer and/or a composition, material, or composition comprising the copolymer composition which is effective for producing some desired therapeutic effect in at least a sub-population of cells in an animal at a reasonable benefit/risk ratio applicable to any medical treatment. A therapeutically effective amount is an amount sufficient to inhibit bacterial survival in at least a subset of cells. Accordingly, a therapeutically effective amount prevents or minimizes disease progression. Disease progression can be monitored relative to an expected disease progression that is based on population studies, controlled observations in individuals, or a combination of both.

The term acrolein derived segment refers to the copolymer segment comprising one or more acrolein monomer residues.

The terms oligomer, polyalkylene glycol oligomer and polyacrolein oligomer refer to polymers consisting of at least two monomer units, preferably at least three monomer units. The oligomers will typically comprise from 2 to 20 monomer units; in one embodiment the number of units is from 2 to 10.

The terms "monomer units" and "monomer residues" refer to units present in the copolymer derived from the reacting monomers such as acrolein and polyalkylene glycol.

The polydispersity index is the ratio of the weight-average molecular weight ($M_w$) of the polymer to the number-average molecular weight ($M_n$) of the polymer. The weight-average molecular weight and the number-average molecular weight of a polymer can be determined by analytical methods, such as high performance liquid chromatography. Once the weight-average and number-average molecular weights have been determined, the polydispersity index is easily calculated by dividing the weight-average molecular weight by the number average molecular weight, $M_w/M_n$. A hypothetically monodisperse polymer has a polydispersity index of 1.000. However, typical commercial polymers, such as the commercially available resins, have a polydispersity index of 10 or more. Polymers with broad molecular weight distributions have higher polydispersity indices and polymers with narrow molecular weight distributions have lower polydispersity indices.

Sepsis is a metastatic infection and inflammatory process that arises when infectious microbes in the circulatory system, including within blood or lymph systems, overwhelms the immune system and the microorganisms can no longer be removed from circulating blood faster than they are proliferating. The most common origins of infections that develop into sepsis are bacteremia, genital-urinary tract infections, pneumonia, cellulitis, wounds and abscesses, sinusitis, meningitis, and surgical procedures (including to the gastro-intestinal tract), or an infected area.

Throughout this specification, use of the terms "comprises" or "comprising" or grammatical variations thereof shall be taken to specify the presence of stated features, integers, steps or components but does not preclude the presence or addition of one or more other features, integers, steps, components or groups thereof not specifically mentioned.

DETAILED DESCRIPTION

The method of treatment comprises administering a copolymer comprising an acrolein derived segment and a polyalkylene glycol oligomer segment (preferably of molecular weight of from 200 to 600 Daltons), the copolymer having a molecular weight of no more than 1500 Daltons, preferably no more than 1000 Daltons.

The acrolein derived segment may comprise one or more acrolein monomer residues. In one embodiment the acrolein derived segment comprises a polyacrolein oligomer.

The polyalkylene glycol may be a poly($C_1$ to $C_4$ alkylene glycol) or mixture or copolymer thereof but in general the polyalkylene glycol is most preferably a polyethylene glycol, preferably of molecular weight in the range of from 200 to 600 Daltons.

It will be understood by those skilled in the art that the term polyethylene glycol preferably does not include diethylene glycol. Polyethylene glycol of average molecular weight 200 to 600 Daltons includes polyethylene glycol of nominal average molecular weight 200 to 600 Daltons wherein the average molecular weight is not more than 110% and not less than 90% (preferably not more than 105% and not less than 95%) of the nominated value. Polyethylene glycol is of formula H—[OCH$_2$CH$_2$]$_n$—OH. The average value of n is at least 3 and is generally from 3 to 13 (although the average need not be an integer). Polyethylene glycol is widely available from commercial suppliers in pharmaceutical grades and is sold in specified nominal molecular weights which generally signify that the average molecular weight is not more than 105% and not less than 95% of the nominated value. The viscosities and methods for molecular weight determination are disclosed in USP NF Official Compendium of Standards Volume 11180-1182 [2007 Edition]. In one set of embodiments the polyethylene glycol is of molecular weight from 200 to 400. In some embodiments it may be preferred to use a specific pure oligomer of ethylene glycol such as the compound of formula H—[OCH$_2$CH$_2$]$_n$—OH where n is 3 or 4.

In one set of embodiments the molecular weight (always meaning herein, the number average molecular weight) of the copolymer is at least 300 Daltons preferably at least 400 Daltons such as in the range of from 400 to 1500 Daltons and more preferably the molecular weight is in the range of from 400 to 1000 Daltons.

The copolymer is particularly suited to treatment of parenteral infections and may be administered by a range of methods suitable for providing effective levels of the copolymer to the site of the parenteral infection. The treatment may be prophylactic, curative or may be conducted to control infection, for example, to allow confirmation of the susceptibility of the pathogen responsible. In one set of embodiments the copolymer is administered directly to a local site of infection such as a skin lesion, wound, lungs, or other site of infection in a specific organ or tissue of the subject.

In another embodiment the copolymer is administered systemically, for example, by oral administration, inhalation, transdermal delivery or by injection such as into the blood stream or intramuscular injection or by intravenous therapy. It is generally accepted that molecules of molecular weight less than about 800 Daltons have reasonably free passage across the abdominal membranes. Oral administration requires that the copolymer is absorbed through the gut wall and into the systemic circulation. In this embodiment it is particularly preferred that the copolymer administered orally is of molecular weight no more than 1000 Daltons such as a molecular weight in the range of from 400 to 800 Daltons. We have found that copolymers of this molecular weight, when administered orally, are transported into the systemic circulation to provide treatment of parenteral infection. The proportion of the copolymer absorbed through the gut wall is generally greater for copolymers of lower molecular weight in this range.

In one set of embodiments the treatment provides protection against infection by bacteria such as methicillin-resistant *S. aureus* (superbugs) as demonstrated in the Examples in a mouse model. The results demonstrate that the efficacy of in vivo kill of bacteria/prophylaxis or therapy following oral administration of the lower molecular weight copolymer such as less than 1500 Daltons and preferably less than 1000 Daltons, such as 400 to 1000 Daltons, provides greater efficacy than higher molecular weight copolymers of of higher molecular weight such as 2500 Daltons (see FIG. 4).

The present invention further extends to (either prophylactic or curative) treatment of infections that have spread into the blood and/or to vital organs. Thus, the invention includes parenteral treatment such as by oral administration or injection into the blood, in particular intravenous injection or therapy, to treat infections that have spread into the blood or vital organs such as kidneys, liver or brain. Such diseases include but are not limited to sepsis, bacteremia and meningitis. The use of IV therapy may be of particular importance where exposure to serious parenteral infection is suspected and/or the condition of the subject to be treated is rapidly deteriorating due to a parenteral infection. For example where sepsis or bacteremia is diagnosed IV therapy with the copolymer, for example as an aqueous or saline solution, may be preferred.

The copolymer may be administered in an pharmaceutically-effective amount to provide local topical treatment at the site of infection and in such cases the dose will depend on the extent and/or severity of the infection such as the extent or severity of a wound infection or the like. The copolymer may be applied as an aerosol, gel, topical foam or ointment or impregnated into a dressing for application to wounds, burns, surgical sites or the like. In a further set of embodiments the copolymer is applied as an inhalation via an aerosol or the like. The inhalation may be used to treat lung infection or to provide systemic treatment via the lungs.

Pneumococcal infection of blood follows pulmonary infection with significant frequency, and can lead to severe complications, such as but not limited to sepsis, bacteremia and meningitis. In one set of embodiments the copolymer is administered as an inhalation such as an aerosol inhalation.

In a further embodiment the copolymer is administered by transdermal delivery from a composition which may comprise a penetration enhancer for the polymer. Patches, microneedles or like devices may be used to enhance transdermal delivery.

In a further embodiment the copolymer is administered by injection, for example intravenous injection.

The copolymer may be formulated in an aqueous composition as it is soluble and remains soluble over the full 1 to 14 range of pH. The copolymer may be administered in compositions with known pharmaceutically-acceptable carriers and excipients; however aqueous formulations provide a significant advantage. The composition may comprise a wide range of concentrations of the copolymer depending on the specific infection to be treated and mode of administration. In one set of embodiments the concentration of the copolymer in an aqueous pharmaceutical composition is in the range of from 0.01% by weight to 20% by weight of the composition. Accordingly, in a preferred set of embodiments the copolymer is administered as an aqueous solution.

The composition may be administered orally in the form of a tablet, caplet, syrup or liquid and the dose administered orally will depend on the severity and type of infection but may be in the range, for example, of from 1 mg to 1000 mg per kilogram of bodyweight per day, such as from 10 mg to 500 mg per kilogram of bodyweight per day.

One of the significant advantages of the copolymer and method of treatment is that they may be used against infections from a wide range of pathogens and in particular is useful in treatment of bacterial infections which may rapidly escalate to present a serious threat such as bacteremia or sepsis or pneumonia or meningitis or cellulitis. Specific examples of such bacterial infections may be selected from the group of bacteria consisting of *Proteus* spp, *Serratia* spp, *Pseudomonas aeruginosa*, *Neisseria meningitidis*, *Escherichia coli*, *Klebsiella pneumoniae*, *Staphylococcus aureus*, coagulase-negative *Staphylococcus* spp, *Streptococcus pyogenes*, *Streptococcus pneumoniae* and *Enterococcus* spp.

The activity against a wide range of pathogens and particularly a wide range of bacteria allows the copolymer to be used as a first line of treatment in serious or life threatening infections where, for example, the severity of the infection may not allow sufficient time to properly identify the responsible bacteria.

The finding herein that acrolein-copolymers are active against parenteral infection was not expected, due to the mechanism of action believed to relate to their activity. Melrose 1996 uses added protein to totally quench the antimicrobial activity of acrolein-polymers. The focus of the prior art has been to treat infections in the gastro-intestinal tract by oral administration of acrolein-polymers having sufficiently high molecular-weights so as to prevent their trans-intestinal migration. Indeed the reactivity of acrolein monomer is such that it has not heretofore been considered to be feasible to polymerize acrolein so as to yield products having molecular weights no more than about 1,000 Daltons. Administration against parenteral infection has also been deliberately avoided for reasons of their potential toxicity (including reaction with serum proteins).

In the prior art preparation of polyacrolein it was considered that the mechanism of polymerization was anionic, and that water content needed to be minimized to avoid quenching of the anion or dissociation of the product. We have now found that the molecular weight may be limited to 1000 Daltons or lower by controlling the ratio of monomers, the dilution of acrolein and polyethylene glycol with water and compared to prior art, keeping the pH in a lower range—maintaining the pH at no more than 12.0 and within a pH range of 12.0 to 7.0. That is, to achieve the new mechanism of polymerization, the pH range is dropped two whole pH units, or 100-fold lower hydroxyl-ion concentration than ever used in prior art polymerizations.

In one set of embodiments the invention provides a method for preparation of a copolymer for treatment of a parenteral infection the process comprising base catalyzed polymerization of acrolein in an aqueous solution comprising polyethylene glycol (preferably of molecular weight of from 200 to 600 Daltons) wherein the ratio of polyalkylene glycol/acrolein is at least 4, preferably at least 8, more preferably at least 10, and water is present in an amount of at least 20% by weight of the composition.

In a preferred set of embodiments the process comprises adding an aqueous solution of acrolein, preferably having an acrolein concentration of no more than 50% w/w, to an aqueous solution of polyethylene glycol comprising at least 10% w/w water and having a pH of no more than 12.0, preferably no more than pH 11.

In a still more preferred embodiment acrolein is added as an aqueous solution to an aqueous solution of polyalkylene glycol of pH 9 to 11.

In general we have found that in the aqueous systems used in the process, a relatively low pH such as no more than 12.0 such as not more than 11.5 (preferably no more than 11) provides significant advantages over the prior art pH range up to pH 14 used to polymerize acrolein. Relatively high pH, as used in the prior art for extended periods, provides oxidation and introduces carboxyl groups which improve solubility. In contrast we have found that solubility is provided in the process of the invention without the need for extended heating at relatively high pH and as a result the carbonyl and/or carboxyl content is very low, typically 0-10% of the copolymer. The minimum carbonyl or carboxyl content is believed to minimize both unwanted reaction with proteins of miscellaneous origins or repulsion to acidic and anionic coatings of germs, thereby in both cases, enhancing antibiotic action.

Without wishing to be bound by theory it is believed that in the process of the present invention polymerization of acrolein in the presence of alkali does not proceed by a totally anionic mechanism in the presence of such significant amounts of water but rather has a significant free-radical mechanism of polymerization.

This conclusion is supported by the facts that: (a) Polymerization was facilitated by the presence of the dual free-radical, oxygen (b) Water which is a major component of the solvent, is anion-quenching (c) Polymerization is significant at ambient temperatures and above—fast, exothermic and inhibited by the typical free-radical inhibitor, hydroquinone—all observations being typical of free-radical polymerization, rather than ionic polymerization (Florey; Odian). Again, without wishing to be bound by theory, it is believed that the reaction mechanism involves formation of initiator-radical between oxygen and hydroxyl ion, followed by radical transfer to polyethylene glycol solvent, thus initiating polymerization; then solvent-transfer termination involving solvent-hydroxyl to limit the number of acrolein residues polymerized at the active radical site, adjacent to the carbonyl within the copolymer.

The polyalkylene glycol oligomer is believed to provide chain-transfer and/or chain-termination, thereby limiting, (together with the aqueous dilution), the molecular weight in direct proportion to the overall hydroxyl-content.

In overview, the core-strategy of the synthesis—and different from that of the prior art (Melrose 2009), is to cause the two segments of the resulting co-polymeric product to be joined by a mechanism which is believed, without wishing to be bound by theory, to proceed by a free-radical mechanism, rather than by a nucleophilic Michael addition. This is done by maximizing the formation of propagating free-radical active-centres (by maximizing the presence of the radical, oxygen)—and by minimizing pH, minimizing the formation of hydrogen-ion deficient active-centres for nucleophilic Michael addition.

The active copolymer antimicrobial was shown by HPLC to have insignificant reaction with either of the amino-acid models cysteine (sulfhydryl) or threonine (hydroxyl), and that the anti-microbial activities of the copolymers can be attributed to a non-covalent, physical hydrophobic effect alone, at the identified proximate carbons within the copolymers, upon the stability of bacterial outer membranes. The mechanism of action in the prior art, which relied on chemical reaction of carbonyl groups in modified polyacrolein with protein, is not therefore believed to be responsible for the anti-microbial activity of the present copolymers.

In contrast with the prior art which teaches the destructive reactivity of acrolein polymers with protein, we have found that the anti-microbial rates of the copolymers are not significantly depressed by the presence of protein. Indeed, for most bacteria, especially *C. difficile*, *S. aureus* and *P. aeruginosa*, net rates of kill (gross kill minus gross growth) were enhanced—even when the protein was a broth, which promoted growth of the target microbe (See Table 2). We have found that the anti-microbial rates of the copolymers are sufficiently fast so as to more than compete with any intra-vascular chemical reactions with protein leading to toxicity, or with in vivo clearing processes. In the perspectives of prior art, consistently, these observations and conclusion are counterintuitive to progressing to synthesize and then use the copolymer (such as the copolymer of Example 1) parenterally, as herein.

We have further found that the copolymers exhibit slower anti-microbial kill-rates against eukaryotic cells such as fungi when compared with the high level of activity found against prokaryotic bacteria. We have noted that vascular and gastro-intestinal cells within mammals are eukaryotic, and this observation is inherent in the design of this invention which seeks selectivity of reactivity by the copolymers, between cells of bacteria and other cells.

The copolymers disclosed herein represent a much-less toxic intra-vascular challenge than acrolein-polymers from prior art. We have found that the copolymers may be prepared with a low polydispersity and that a low polydispersity of preferably less than 5, more preferably less than 2, and most preferably less than 1.5, still more preferably less than 1.2, enhances the performance of the copolymer, particularly where the molecular weight is less than 1000, such as from 400 to 1000 Daltons, more preferably 400 to 800 Daltons such as 400-600 Daltons. The polymers of the present invention may be prepared as a narrow symmetrical and single polymer with polydispersity index of approximately 1. Previously described acrolein polymers generally contain a higher polydispersity, or in the case of the polymer of Example 6 of WO 09/059350, contain, on very sensitive UV detection, about 1% and about 8 times more of a wide range of lower molecular weight polymers/residues, which are not readily detectable from refractive index detection. The copolymers herein may be formed quantitatively, in narrow molecular weight distribution of polydispersity near unity. The copolymers contain much fewer potentially toxic contaminants (side-products and starting materials, including residual, lachrymatory acrolein) than heavily heated and autoxidized acrolein-polymers of earlier art. In the preferred embodiment of the invention, both carbonyl content and the pH used in preparation by base catalyses are at an unprecedented minimum—and both factors may be used to minimize side-products and their potential toxicity from particularly, Cannizarro reaction with carbonyl, and which prior art has found to be abnormally rapid in acrolein-polymers.

The copolymer has been found to have active anti-microbial activity against a site, which is common to all bacteria—regardless of mutation. This conclusion is drawn from the results from a range of representative bacteria in Table 2 (which illustrates that the copolymers have the same antimicrobial rate-activity regardless of the bacteria being in natural or mutated-superbug form), and Table 3 (which illustrates that resistance did not occur regardless of mutation which caused inactivity in Amoxicillin, from repeated use). This represents a new, general and successful method of treatment and prevention of infection in a subject, from bacteria of all types and which exhibit the propensity to develop antimicrobial resistance.

In addition to acrolein monomer, other monomers e.g., acrylic acid, acrylamide, acrylonitrile, vinyl chloride, styrene, methacrylic acid, methyl methacrylate, vinyl acetate, vinyl pyridine and vinyl pyrrolidone may be used as additional monomers in preparation of copolymers comprising a polyalkylene glycol oligomer segment and acrolein derived segment, as described herein. The additional monomers may be present in amounts which are not adverse to the antimicrobial activity of the copolymer. The ratio of monomers may be chosen so as to maintain the water solubility of the copolymer and incorporation of other monomers may be controlled by reaction conditions and relative monomer concentrations bearing in mind monomer reactivity. In general it is preferred that other monomers constitute no more than 15 mole % of the monomer residues of the copolymer, preferably no more than 10 mole % and most preferable the copolymer only consists of polyalkylene glycol and acrolein monomer residues.

The hydrophobic mechanism, which is characteristic of the copolymers of the invention, is achieved through the process steps, which provide control over: molecular weight; affinity for antimicrobial-reaction with bacterial cells, over eukaryotic cells; enhanced antibacterial activity in the presence of protein; and minimization of both carbonyl and carboxyl-contents within the copolymers.

The copolymer antibiotics provided herein generally provide efficacy against a wide range of bacteria, whether resistant or non-resistant, and provide activity with certainty. The activity may or may not exceed the activity of specific antibiotics against certain specific bacteria—but herein, the certainty of antibiotic activity against the range of bacteria, especially resistant bacteria as implicated in the contemporary, serious escalation of infectious disease, provides greater and valuable confidence for the appropriate treatment of bacterial infections of all types. The same level of confidence with conventional antibiotics requires firstly, a determination of the identity and pathology concerning the bacteria present in the infection—and only then, a selection from the remaining active antibiotics.

In a preferred set of embodiments the method of preparation of copolymers of the present invention comprises the following steps:

providing a mildly basic (preferably of pH no more than 12.0; more preferably of pH 9 to 11) aqueous solution of a polyalkylene glycol (preferably polyethylene glycol of molecular weight in the range of from 200 to 600 Daltons);

stirring the mildly basic solution vigorously to entrain air; adding (preferably slowly over a period such as at least 2 minutes, more preferably at least 5 minutes) acrolein as an aqueous solution of concentration no more than 50% w/w of the acrolein aqueous solution (usually containing preservative);

maintaining the reaction temperature in the range of from 10° C. to 40° C.;

and once the acrolein monomer has been consumed, adding acid to provide a pH less than 9 and preferably no more than 8.

The molecular weight of the resulting copolymer is controlled by the molecular weight of the polyalkylene glycol, as well as being directly proportional to its hydroxyl concentration. (The polymerization begins at ambient temperature, then rises slightly as the exothermic polymerization—which is evident from the appearance and then disappearance of yellow color from the preservative, progresses.)

During the reaction the stirring is preferably continued, and the pH maintained mildly basic (preferably of pH no more than 12.0, more preferably of pH 9 to 11), only as necessary. The addition of more base and its concentration is minimized so as to lower degradation/side-reactions and to reduce carbonyl or carboxyl formation in the product.

Finally, the pH of the solution may be reduced. In a preferred set of embodiments, the pH is adjusted to near neutral, by the addition of acid. The extremely pungent smell of acrolein is no longer evident in the copolymer product, which is formed in at least 99% yield.

The resulting acrolein-copolymers typically have molecular weights in the range of from 250 to 1000 Daltons (such as 300 to 1000 Daltons, 400 to 1000 Daltons or 400 to 800 Daltons). The copolymers are free of turbidity which would be expected from any content of polyacrolein. Content of, and bonding between the acrolein derived segment and the polyethylene glycol oligomer segment, in the manner proposed earlier, is demonstrated by the size separation-HPLC of all copolymers—each having one-single, narrow, symmetrical, dominant and unresolvable mass-peak—without indicating either residual acrolein monomer or substantial polyacrolein; furthermore, the copolymer MW 1,000 from Example 2, contrary to the resolvable change and expectation if the association between the segments was merely physical inter-adsorption—did not change in size separation-HPLC, nor antimicrobial activity, after equilibration with polyethylene glycol MW 200 under basic conditions comparable to those used in the original preparation of all the copolymers. (See Example 2).

The weight-ratio of acrolein:polyethylene glycol used in its preparation of the copolymer is preferably between 1:4 and 1:40, and more preferably between 1:8 and 1:20.

The preferred base is an aqueous solution of an alkali hydroxide; more preferably, the alkali hydroxide is sodium hydroxide.

The preferred acid is dilute hydrochloric acid—although acetic acid is useful for pH buffering purposes.

It is preferred that the addition of acrolein to the aqueous solution of polyalkylene glycol takes about 10 minutes—and the reaction to completion, and the addition of acid generally takes place about 40 minutes, and preferably is no more than 90 minutes.

Typically we have found that a reaction time of 50 minutes is suitable to obtain virtually complete conversion to the copolymer product.

The acrolein is preferably added to the aqueous polyalkylene glycol as an aqueous solution—more preferably as a concentration in the range of from 10% to 30% by weight of acrolein monomer, based on the weight of the aqueous acrolein solution to be added to the aqueous polyalkylene glycol solution.

The resulting copolymer has a reactive carbonyl group-content (plus any carboxyl-content) of less than 10%, more preferably less than 5%, and still more preferably zero %.

The acrolein solution usually contains inhibitor, hydroquinone such as no more than 0.5% and typically 0.01 to 0.5% and more preferably 0.1% w/w.

It will be apparent to those in the art that the copolymers herein may be included in a variety of compositions and physical forms. Particularly, compositions and pharmaceutical methods of use, in vivo, will be apparent, taking advantages of slower clearances of the copolymer. Also, it will be apparent that pharmacological advantage may be taken of variance in molecular weight to adjust the rate of penetration through membranes, tissues and organs—and the resultant absorption or distribution within human or animal; in this context, the lower molecular weight copolymers such as, for example 400 to 800 Daltons, than copolymers over a molecular weight of 1000 Daltons.

In view of the results herein, it is also conceivable to add protein, particularly broth to enhance in-use antimicrobial activity of the copolymers.

The subject products, herein, are aqueous-soluble and administration to humans/animals may be by the usual methods known in medicine—particularly, by mouth or injection—and are able to be used in any practical pharmaceutical way, alone or in compositions, within organs and tissues, or in contact with or in in vivo vascular systems of either humans or animals. When the copolymers are administered to humans and animals, they can be given per se or as a pharmaceutical composition containing, for example, 0.1% to 99.5% (more preferably, 0.5% to 90%) of active ingredient in combination with a pharmaceutically-acceptable carrier.

Compositions may be solids, solutions, gels, emulsions or suspensions of matter comprising a pharmacologically effective amount of the copolymer.

The copolymers and their compositions have substantial in vitro anti-microbial activity against particularly, bacteria *Staphylococcus aureus, Streptococcus pyogenes, Escherichia coli, Pseudomonas aeruginosa* but lesser activity against fungi *Aspergillus brasiffiensis* and *Candida albicans*.

Of particular significance because of global problems of bacterial resistance to antibiotics, the copolymers have more anti-microbial stability than Amoxycillin to repetitive exposure to either *E. coli, S. aureus* or *P. aeruginosa*. The copolymers, without exhibiting any unusual resistance from successive generations of the bacteria, normally and routinely killed "superbugs" of *E. coli, S. aureus* and *P. aeruginosa*.

The minimum kill concentrations for these three bacteria *E. coli, S. aureus* and *P. aeruginosa* was in the practical range 1-200 ppm of copolymer.

EXAMPLES

The invention will now be described further with reference to the following Examples.

It is to be understood that the examples are provided by way of illustration of the invention and that they are in no way limiting to the scope of the invention.

Figure 1:
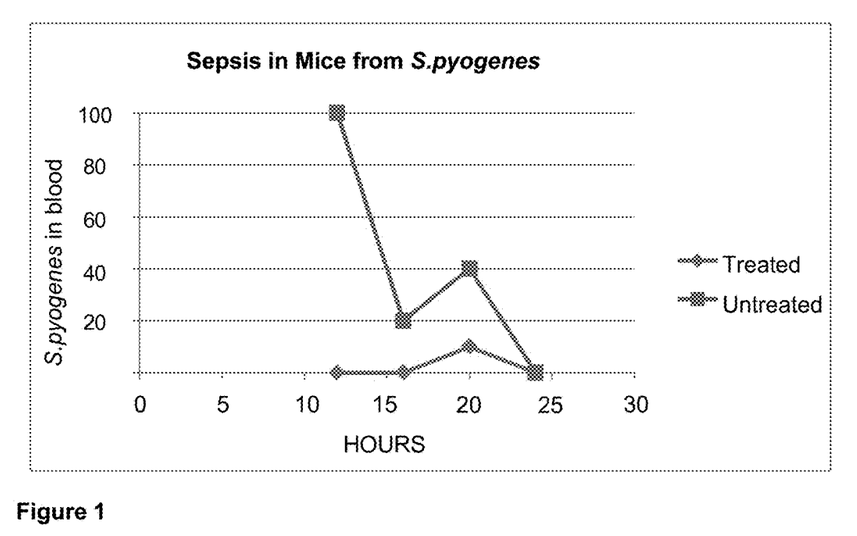
FIG. 1 is a graph of the percentage-ratio of incidence (cfu/mL) of *S. pyogenes* in the blood of two sets of ten mice 12 to 24 hours after infection with the bacteria in accordance with the experimental procedure of Example 5. One set of mice being treated with the copolymers of Comparative Example 1 at a time 15 minutes after infection and the other set being untreated (negative control) receiving saline in place of the treatment.
Figure 4:
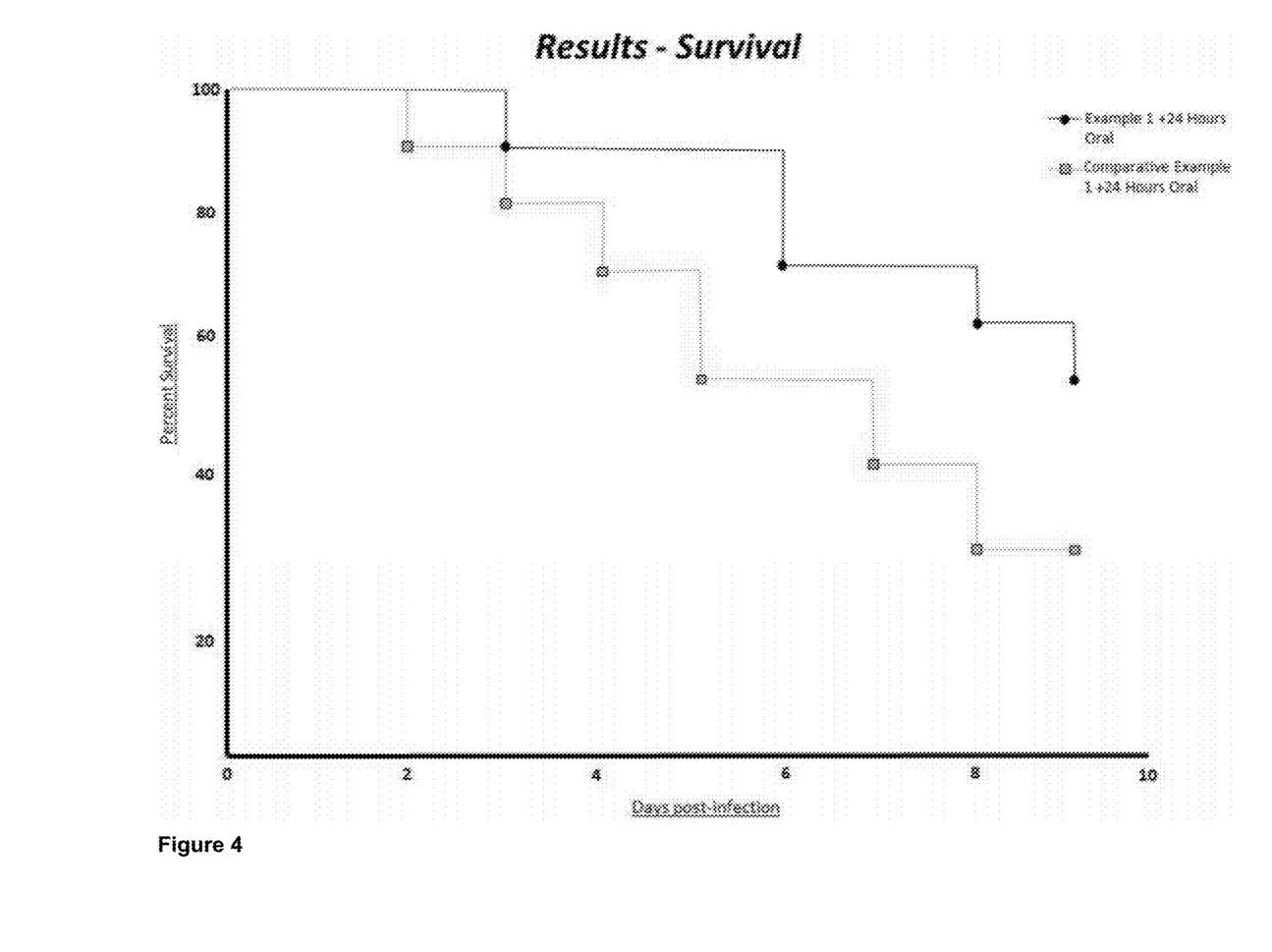
FIG. 4 is a graph of mice culled due to morbidity or mortality among two groups of each 10 mice, infected with *S. aureus* superbug (*S. aureus* USA300), and 24 hours afterwards each group treated curatively with respectively, copolymer MW 500 Example 1 at 132 mg/Kg of mouse, or copolymer MW 2500 Comparative Example 1 at 167 mg/Kg of mouse. The experimental procedure is reported in Example 8.

The copolymers from Example 1 and Comparative Example 1 have anti-microbial characteristics of Minimum Kill Concentration, broad spectrum rates of kill—faster in the presence of protein-broth, and resistance to the development of superbugs to them. (See Tables 1, 2 and 3). In the context of delivery by adsorption through pulmonary membranes, it is of interest that the low MW copolymer is able to kill *Micobacterium fortuitum*—a model for bacteria causing tuberculosis copolymer MW 2500 from Comparative Example 1, in vivo is anti-microbial active (FIGS. 1 and 4).

However, it is noteworthy from Table 2 that although it often has faster/more active in vitro anti-microbial activity than the lower MW 500 from Example 1—in vivo always— either prophylactically or curatively, (e.g. in experiments giving rise to FIGS. 4 and 5), its performance was markedly more sluggish—and the smaller copolymer effective or more than the positive control. That is, synthesis and use of the lower molecular weight copolymer according to this invention has given a significant attribute and advantage over the copolymer from Comparative Example 1; furthermore, this attribute and advantage of the smaller copolymer in vivo is counter-intuitive to prior art, and to the initially-made in vitro tests showing superiority of the bigger copolymer, and described in this paragraph.

In vivo within mice, at a confidence level $p>0.01$, the copolymer from Example 1, MW 500, after a single dose of 132 mg/kg of mouse, effectively killed superbug Methicillin Resistant *S. aureus* USA300 in a protocol involving both prophylactic and curative anti-microbial activity in the subjects' blood and kidneys; it illustrates the application of prophylactic protection in the blood, in the early hours before the germ has spread as an infection in its preferred site (the kidneys), whence curative therapy occurs. (See FIG. 1).

MICROBES

The microbes used experimentally in this invention, and provided by ThermoFisher Scientific (Australia) were *Escherichia coli* (atcc 25922), *Pseudomonas aeruginosa* (atcc 27853), β-Lactam resistant *Klebsiella pneumoniae* (atcc 700603), *Staphylococcus aureus* (atcc 25923), Methicillin resistant *S. aureus* (atcc 43300), *Streptococcus pyogenes* (atcc 19615), *Enterococcus faecalis* (atcc 29212), Vancomycin resistant *E. faecalis* (atcc 51299), *Clostridium difficile* (atcc 9689); *Microbacterium fortuitum* (atcc 6841); *Aspergillus brasiffiensis* (atcc 16404) and *Candida albicans* (atcc 10231).

Estimates of Carbonyl Content

The estimates of carbonyl content reported herein are based upon an established method (Peters 1962; Melrose 2009). In duplicate, an aqueous sample-solution of copolymer (1 g) was weighed to an accuracy of 0.01 g—water (9 g) was added, and then the solution was brought to pH 6.00 by the addition of either 0.01M hydrochloric acid or 0.01M aqueous sodium hydroxide, as appropriate.

A 1% solution of hydroxylamine hydrochloride (50 mL) was brought to pH 6.00 with 0.01M aqueous sodium hydroxide.

The above solutions of copolymer and reagent were mixed, and stood at room-temperature for 30 minutes; the reactants were then back-titrated with 0.01M aqueous sodium hydroxide (V mL) to pH 6.00.

Thus, the w/w % carbonyl-content of the original sample-solution (W g) was estimated as acrolein, equals: V×0.10× 5.6/W.

Quantitative Analysis of Copolymer by HPLC

High Performance Liquid Chromatography (HPLC) was performed on Shimadzu Prominence equipment using simultaneously, both refractive-index and UV (268 nm) detectors; the column was either or both (in series) Waters Hydrogel 120 or Waters Hydrogel 250, for separation by size-exclusion.

MW calibration was done by a straight-line plot of exclusion-time versus log MW of Sigma-Aldrich polyethylene glycols of average MW range 200 to 10,000 Daltons. Thus, it follows from the method of determination that the molecular weights of acrolein-copolymers which were always determined on this basis and reported herein— always refer to a Number Average Molecular Weight (corrected to the nearest 500 Daltons).

Separations were performed on aqueous solutions of solute (0.020 mL; 0.4% w/w), with water-solvent (0.6 mL to 1.0 mL/minute).

Quantitative Analysis of Copolymer by Mass Spectrometry

Two separate techniques (by courtesy of Shimadzu Scientific Instruments (Oceania) Pty Ltd) were performed:
  Direct injection into the mass spectrometer, without prior chromatography;
  Mass spectrometry, after prior chromatography
Equipment; experimental conditions were: Nexera UHPLC Binary High Pressure Gradient, and LCMS-8060 (run under Q3 scans to simulate single quadrupole mass spectrometry; mobile phase equal parts 0.02% formic acid in water, and 0.02% formic acid in acetonitrile, and column Phemonenex Aeris XB C18 300A 150×2.1 mm.

Quantitative UV/Visible Analysis of Polymer Solutions

Solutions for analysis were prepared by dilution of copolymer (250 mg) in water (20 g) and then if applicable, a stoichiometric molar equivalent of reactant; then, diluted 1:9 with water before taking the UV spectrum on Shimadzu UVmini-1240 equipment.

Example 1 and Comparative Example 1

This Example describes preparation of a copolymer of the invention of molecular weight of about 500 Daltons, comprising a polyacrolein oligomer segment, and a polyethylene glycol oligomer segment of molecular weight 200 Daltons. The copolymer is purposefully illustrated from a preparation at pH 12.0, as this is the highest pH recommended for reliable success, without introducing levels of unwanted side-reactions as described herein. The anti-microbial activity of the copolymer is compared with that of a corresponding copolymer of molecular weight approximately 2500 Daltons.

Example 1—Preparation of Copolymer of MW about 500 Daltons

A solution of freshly distilled acrolein (5 g; inhibited with hydroquinone 0.1% w/w) in water (20 g) was slowly added over 10 minutes to a solution of water (20 g) and polyethylene glycol (60 g; MW 200) which had been rendered pH 12 by the addition of 1M aqueous sodium hydroxide; during the 10 minutes, the yellow color of oxidized hydroquinone quickly appeared, then disappeared. During the process the composition was continuously and vigorously stirred to provide copious contact with air. An exothermic and rapid polymerization took-place, and the temperature of the reactants was maintained between approximately 25° C. and 35° C.

After another 50 minutes, the clear solution was adjusted to pH 7.5 by the addition of 1M aqueous hydrochloric acid; the product was a clear, almost colorless (very pale yellow) solution. All the tests done on the sample and the results herein, were done on a sample without any purification and having been stored for 4 or 6 years at 7° C.; this is taken as indicative of the high purity and high stability of the product.

The UV-visible, 200-600 nM spectrum of the product only had substantial absorption in the far edge of the 200-300 nM region. This is consistent with negligible content of unsaturation conjugated with carbonyl and which may be associated with propensity for a Michael Reaction HPLC indicated the polymerization-yield was 99-100% w/w, and any residual acrolein-monomer was less than 1 ppm w/w; MW was approximately 500 Daltons. Mass spectrometry showed base a base-peak of 312, and indicating the copolymer comprised five oxyethylene (ex PEG) residues covalently joined linearly to two 2-propanal (ex acrolein) residues.

When tested down to pH 1 (and up to pH 14), the copolymer remained soluble. The copolymer has approximately 0-10% w/w carbonyl-content or carboxyl-content.

The single peak of the product in HPLC remained narrow and unresolved whether HPLC was done in water at 1 ml/minute, over Waters Hydrogel 120, Waters Hydrogel 250 singularly or in series of either, alternate sequence.

The same preparative results occurred when the polymerization was conducted at either pH 8 or pH 10, and always with exactly the same in vitro microbiological rate-results against *E. coli*, and same HPLC results (except pH 8 gave a product having an amount of materials indicative of dimers or oligomers of acrolein of total amount less than 1% w/w; in vivo microbiological rate tests were the same for all products.

The preparation of Example 1 was independently repeated a number of times, at various pHs between 8 and 12, including separately pH 8, pH 10 and pH 12 by another member of the applicants' laboratory, and gave identical polymerization results, HPLC and in vitro rate-test results against *E. coli*.

Comparative Example 1—Copolymer of Molecular Weight about 2500 Daltons

This Example describes preparation of a copolymer, not of the invention, of higher molecular weight, 2500 Daltons comprising a polyethylene glycol segment of molecular weight 2000.

A solution of freshly distilled acrolein (5 g; inhibited with hydroquinone 0.1% w/w) in water (20 g) was slowly added over 10 minutes to a solution of water (30 g) and polyethylene glycol (20 g; MW 2,000) which had been rendered pH 11 by the addition of 1M aqueous sodium hydroxide; during this period, the yellow color of oxidized hydroquinone quickly appeared, and then disappeared. The composition was vigorously mechanically stirred prior to and during addition to provide copious contact with air. An exothermic and rapid polymerization took place, with the temperature maintained between 25° C. and 35° C.

After stirring during an additional 50 minutes, the clear solution was adjusted to pH 7.5 by the addition of 1M aqueous hydrochloric acid; the product was a clear, almost colorless (very pale yellow) solution.

It is noteworthy that in common with all polyacrolein-products in prior art, agar-diffusion techniques of microbiological analysis are not used herein, due to resistance by relatively high molecular weight products to diffusion through agar.

All the tests done on the sample and their results recorded herein, were done on a sample without any purification and having been stored for 4 to 6 years at 7° C.; this is taken as indicative of the high purity and high stability of the product.

The UV-visible, 200-600 nM spectrum of the product only had substantial absorption in the far edge of the 200-300 nM region.

HPLC indicated the polymerization-yield was 99 to 100% w/w, and any residual acrolein-monomer was less than 1 ppm w/w; MW was approximately 2,500 Daltons. When tested down to pH 1 (and up to pH 14), the polymer remained soluble. The polymer has approximately 0-10% w/w carbonyl-content.

The single peak of the product in HPLC remained narrow and unresolved whether HPLC was done in water at 1 ml/minute, over Waters Hydrogel 120, Waters Hydrogel 250 singularly or in series of either alternate, sequence.

Based upon the polymerization mechanism described herein, It may be calculated that equivalents of acrolein monomer added in the polymerization (in relation to equivalents of polyethylene glycol) are greater in the case of Comparative Example 1, than Example 1, and therefore any propensity to form any insoluble polyacrolein is greater in the former, but was not observed, even after standing at 7° C./6 years. Stepwise acidification of a dilute solution of the acrolein-polymer to pH 2.5 with dilute hydrochloric acid—and back-titration with dilute sodium hydroxide solution demonstrated the absence of carboxyl groups ($pK_a$=4.5).

Estimate of Minimum Kill Concentration of Copolymers from Example 1 and Comparative Example 1

Serial dilutions of the copolymer were made. In duplicate, each dilution was then inoculated with bacteria to achieve an approximate concentration $10^6$ cfu/m L, and incubated at pH 6.5 to 7.0, 37° C. for 24 hours.

A 1 mL aliquot was removed from each respective solution and mixed for one minute with a 1 mL aliquot of Trypticase Soy Broth, then 8 mL of sterile water was added and mixed. Aliquots (1 mL) were then removed from each solution and lawn-inoculated via flooding onto Horse Blood Agar plates, for 24 or 48 hours incubation at 37° C. Visual counts of bacterial growth (colony forming units; cfu) on the plates were performed.

The minimum kill concentration of the copolymers of Comparative Example 1 and Example 1 were determined against a range of bacteria and the results are shown in Table 1.

TABLE 1

| | Minimum Kill Concentrations | |
|---|---|---|
| | Copolymer (Example 1) | Copolymer (Comparative Example 1) |
| *S. aureus* | 10 ppm | 1 ppm |
| *S. pyogenes* | | 20 ppm |
| *E. coli* | 10 ppm | 10 ppm |
| *P. aeruginosa* | | 200 ppm |
| *E. faecalis* | | 150 ppm |

The Microbiological Assay of each composition was unaltered upon either aging at 8° C./4 years, or exposure to the simulated acidic conditions within the stomach (See Example 4).

Each of the copolymers of Example 1 and Comparative Example 1 has substantial in vitro anti-microbial activity against bacteria *Staphylococcus aureus, Steptococcus pyogenes, Escherichia coli, Pseudomonas aeruginosa* but lesser activity against fungi *Aspergillus brasilliensis* and *Candida albicans*.

Both copolymers were still stable after four years at 8° C., and were stable to simulated pH conditions during residence time in the human stomach.

Viable micro-organism (to result in approximately 10×E6 cells per mL) was added to an aqueous solution of copolymer of Example 1 (383 mg; 5.4% w/w on acrolein) or copolymer of Comparative Example 1 (303 mg; 6.7% w/w on acrolein) in sterile water (20 mL), pH 6.5 to 7.0; a control solution did not contain any acrolein-product. Optionally, Trypticase Soy Broth (1 mL) was immediately added to the reactants.

At time intervals, after mixing an aliquot (1 mL) with an equal volume of Trypticase Soy Broth growth medium for 1 minute, and then water (8 mL)—an aliquot (1 mL) was streaked or lawn-inoculated on agar growth-plates, incubated at 30° C. or 37° C. for 24 to 48 hours, and CFUs counted.

The results are shown in Table 2.

TABLE 2

Rates of Kill of Microbes

| | Copolymer (Example 1) | | Copolymer (Comparative Example 1) | |
|---|---|---|---|---|
| | Without broth | With broth | Without broth | With broth |
| S. aureus | 1-3 hours | 1-3 hours | 20-60 mins | 20-60 mins. |
| S. pyogenes | 20-60 mins. | 20-60 mins. | 20-60 mins. | 20-60 mins. |
| E. faecalis | | 1-3 hours | | 1-3 hours* |
| E. coli | | 20-60 mins. | 20-60 mins. | 20-60 mins. |
| P. aeruginosa | | 3-24 hours | | 3-24 hours |
| C. difficile | | | >2 hours | 20-60 mins. |
| C. albicans | | >24 hours | | 3-24 hours |
| A. brasilliensis /Superbugs | | >24 hours | >2 hours | 3-24 hours |
| MRSA (S. aureus) | | 1-3 hours | | 20-60 mins |
| VRE (E. faecalis) | | 24 hours | | 1-3 hours |
| K. pneumoniae | | 1-3 hours | | 20-60 mins |
| S. aureus ex Table 3 | | 1-3 hours | 1-3 hours | 20-60 mins |
| #M. fortuitum | | >24 hours | | 3-24 hours |
| E. coli ex Table 3 | | 20-60 mins. | 20-60 mins. | 20-60 mins |
| P. aeruginosa ex Table 3 | | 20-60 mins | 3-24 hours | 20-60 mins. |

*Based upon colony morphology, markedly more rapid than Example 1
M. fortuitum is a bacterium used as a model for study of Mycobacterium tuberculosis and tuberculosis.

(The anti-microbial activities of the copolymers increased with pH, so all observations were made between pH 6.5 and 7.0—a pH about half a unit below that of any encountered during parenteral sepsis of any type; also, this was quite naturally attained and therein avoided the complications of interactions with a variety of added salts from different buffers.)

Example 2

This example demonstrated preparation of a copolymer of the invention of molecular weight of about 1000 Daltons comprising a polyethylene glycol oligomer segment of molecular weight 600 Daltons.

A solution of freshly distilled acrolein (5 g; inhibited with hydroquinone 0.1% w/w) in water (20 g) was slowly added over 10 minutes to a solution of water (20 g) and polyethylene glycol (60 g; MW 600) which had been rendered pH 10 by the addition of 1M aqueous sodium hydroxide. The composition was vigorously stirred before and during the addition of acrolein to entrain air and provide copious contact with air, an exothermic and rapid polymerization resulted and the temperature was maintained between about 25° C. and 35° C. After commencement of the addition the yellow color of oxidized hydroquinone quickly appeared and then disappeared resulting in a clear solution.

After another 50 minutes, the clear solution was adjusted to pH 7 to 8 by the addition of 1M aqueous hydrochloric acid; the product was a clear, almost colorless (very pale yellow) solution. (The UV-visible, 200-600 nM spectrum of the product only had substantial absorption in the far edge of the 200-300 nM region.)

HPLC indicated the polymerization-yield was 99-100% w/w, and any residual monomer was less than 1 ppm w/w; MW was approximately 1,000 Daltons. When tested down to pH 1 (and up to pH 14), the copolymer remained soluble. The polymer has approximately 0-10% w/w carbonyl-content.

In vitro the copolymer killed, without broth, E. coli in 3 hours.

The copolymer has substantial in vitro anti-microbial activity against bacteria S. aureus and E. coli. The Microbiological Assay was unaltered upon either aging at 8° C./48 months.

Polyethylene glycol MW 200 (120 mg) was added to the copolymer (383 mg), then one drop of 1M sodium hydroxide to bring the pH to 11; after standing at ambient temperature for 2 hours, the pH was adjusted to 7.5 with a drop of 1M hydrochloric acid, and stood 3 days. Neither the HPLC nor the antimicrobial activity of the copolymer changed as the result of this treatment.

Example 3

This Example examines the activity of the copolymers of Example 1 and Comparative Example 1 following repetitive activity against bacteria, to examine the propensity of the bacteria to develop resistance (See Table 3).

Three test organisms—E. coli, S. aureus and P. aeruginosa—were respectively inoculated to achieve an approximate concentration $10^6$ cfu/mL in the test solutions; the test solutions each comprised 19 g sterile distilled water, 1 mL trypticase soy broth and copolymer (Example 1; 383 mg; 5.4% w/w on acrolein added) or Comparative Example 1; 303 mg; 6.7% w/w solution on acrolein added). The inoculated test solutions, pH 6.5 to 7.0 were then incubated at 37° C. for sufficient time-periods such that approximately $10^2$-$10^3$ cfu/mL (or 99-99.9% of organisms) killed was achieved.

A 1 mL aliquot was removed from each respective solution and mixed for one minute with a 1 mL aliquot of Trypticase Soy Broth, then 8 mL of sterile water was added and mixed. Aliquots (1 mL) were then removed from each solution and lawn-inoculated by flooding onto Horse Blood Agar plates for 24-48 hours incubation at 37° C. Visual counts of bacterial growth on the plates were performed.

Successive generations of E. coli, S. aureus or P. aeruginosa respectively were cultivated via their selection through repeated exposure to a copolymer or Amoxicillin; Organisms surviving treatment were harvested for another cycle of treatment—this process being repeated up to 25 times.

Both copolymers of Example 1 and Comparative Example 1 continued to achieve a normal reduction of approximately $10^2$-$10^3$ cfu/mL (or 99-99.9% of organisms) killed against up to 25 successive generations of *E. coli, S. aureus* and *P. aeruginosa*, respectively, and in each case, without any sign of increasing resistance to the anti-microbial activity of the copolymers; rates of antimicrobial kill of generation 1 and generations of their derived superbugs, when compared, were the same.

This is considered to be a particularly demanding method of assessing the propensity of the bacteria to develop resistance to the antibiotic. If reduction of counts is a magnitude of $10^3$ for each of 25 cycles—the resultant germ may be considered to be the most resistant by a selection of 1 in $10^{75}$.

Parallel studies comparing similar treatments of *E. coli* and *S. aureus*, respectively with a 0.35% w/w solution of Amoxicillin antibiotic resulted in bacterial resistance after the second and eighth generation, respectively. The acrolein-copolymer product had normal antimicrobial rates against each of these generated "superbugs".

The results are shown in Table 3.

TABLE 3

Number of generations of microbes to resistance

| | Copolymer (Example 1) | | Copolymer (Comparative Example 1) | |
|---|---|---|---|---|
| | Without broth | With broth | Without broth | With broth |
| S. aureus | >12 | | >25 | >11 |
| Amoxicillin | | | 8 | 10 |
| E. coli | >25 | | >25 | |
| Amoxicillin | | | 2 | 8 |
| P. aeruginosa | >25 | | >25 | >9 |
| Amoxicillin | | | | 6 |

Comparative Example 2—Hydrophobic Anti-Microbial Activity of Polyethylene Glycol (PEG)

An anti-microbial activity by a physical hydrophobic mechanism (from added PEG, only) was demonstrated by incubating at 37° C., 20 g water, 0.299 g of a 30% w/w solution of PEG 2000, pH 6.5 and 10e6 cfu/mL of *E. coli* for time intervals of 0 minutes, 60 minutes, 24 hours and 48 hours, respectively; kill was observed at 48 hours.

Example 4—In Vitro Simulation of Acidic Resident-Conditions in the Stomach

In duplicate, the aqueous solution of copolymer (1.00 g) was added to water (9 g) and then made pH 2 by the addition of 10% hydrochloric acid; also in duplicate, as the blank, an aqueous solution of copolymer (1.00 g) was treated similarly—but substituting the same volume of water for the hydrochloric acid.

All were heated at 37° C./4 hours—then, adjusted to pH 6.5 to 7.0, before analysis of their physical, chemical or microbiological properties.

Examples 5 to 9—In Vivo Experiments

All experiments were prior-audited, and then supervised to comply with international standards to ensure humane treatment of the animals. All experiments were performed in independent laboratories. In particular, all experiments in Examples 6, 7 and 8 were done in USA within pre-designed protocols specifically to research sepsis and bacteremia; protocols were "blinded" of the identity of test-solutions, to both the supervisor and assistants. All infections were in 100 µL, designed to result in approximately $10^7$ cfu/mL infection of mouse-blood; mice were type BALB/c—ten per group in each experiment. Mice were assessed by either sacrifice followed by cfu/g count of bacteria within organ(s), or within a 1 to 7 scale of Health Score, including (1; alert and healthy) to (5; sick and very ruffled coat; euthanized) to (7; deceased). The protocols are tabulated, and follow.

Example: 5

This example examines the in vivo activity of the copolymer of Comparative Example 1 and the clearance of bacteria from the blood over 24 hours.

A preliminary experiment was conducted with copolymer MW 2500; Comparative Example 1; 167 mg/Kg of mouse. Two sets of 10 mice were used; one set being the treatment set and the other an untreated set. Both sets of mice were infected with *S. pyogenes* by tail injection. 15 Minutes after infection the treatment set of mice received a tail injection of the copolymer of Comparative Example 1 and the untreated set received saline instead of the treatment. The percentage-ratio of incidence (cfu/mL) of *S. pyogenes* in the blood of treated and untreated sets of mice were monitored from 12 to 24 hours after infection and the result are shown in FIG. 1.

Summary

Route of treatment: Tail-injection

Time the treatment was before/after infection: 15 minutes after

Test-treatment by copolymer: Comparative Example 1; 167 mg/Kg

Negative-control by:

Route of infection: Tail-injection

Infection by: *S. pyogenes*

For results, see: FIG. 1

FIG. 1 demonstrates firstly, that the copolymer, in vivo is antimicrobial-active, and secondly, that the bacteria clears naturally from the blood within twenty-four hours (It was determined elsewhere, by assay, to the kidneys).

Example: 6

This Example examines the in vivo activity of the copolymer of the invention of Example 1 against antibiotic resistant bacteria and compares the activity with a positive control (Oxacillin) and negative control (saline).

Figure 2:
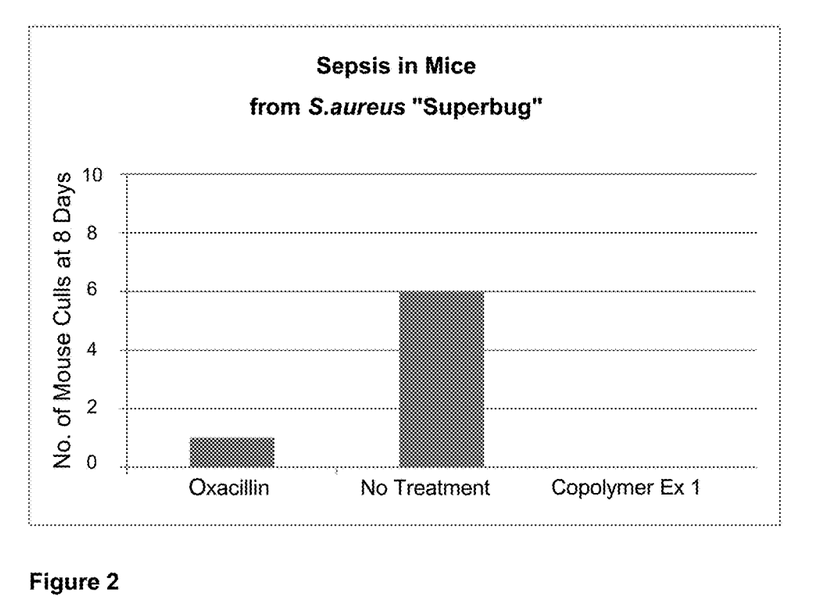
FIG. 2 is a column chart comparing cull rates after 8 days, of mice within 3 groups, each of 10 mice, in accordance with the experimental procedure of Example 6. 10 Minutes before infection with *S. aureus* superbug (*S. aureus* USA300) the three sets of mice received the copolymer of the invention of Example 1 MW 500; 132 mg/Kg of mouse, positive control Oxacillin, 500 mg/Kg and negative control, saline respectively.

The copolymer of the invention MW 500; Example 1; 132 mg/Kg of mouse, positive control Oxacillin, 500 mg/Kg and negative control, saline were administered by tail injection to three groups of 10 mice before infection by tail injection with *S. aureus* superbug (*S. aureus* USA300). Over the following 8 days, the cull rates of mice within the 3 groups were recorded. The figure demonstrates that the copolymer, in vivo is antimicrobial-active against *S. aureus* superbug.

The results of the Example are shown in FIG. 2.

Summary

Route of treatment Tail-injection

Time the treatment was before/after infection: 10 minutes before

Test-treatment by copolymer: Example 1 (Ex 1); 132 mg/Kg

Negative-control by: Saline
Positive-control by: Oxacillin; 500 mg/Kg
Route of infection: Tail-injection
Infection by: MRSA (*S. aureus* USA300)
For results, see: FIG. 2.

Example: 7

This Example examines the efficacy of the copolymer of the invention of Example 1 in treatment of infection with antibiotic resistant bacteria and the safety of the copolymer for parenteral administration.

Two groups of 10 mice each, both treated with copolymer MW 500; Example 1 (Ex 1); 132 mg/Kg of mouse; one ("infected") group of mice was infected with *S. aureus* superbug (*S. aureus* USA300) and the second ("not infected") group was not infected with the bacteria.

Figure 3:
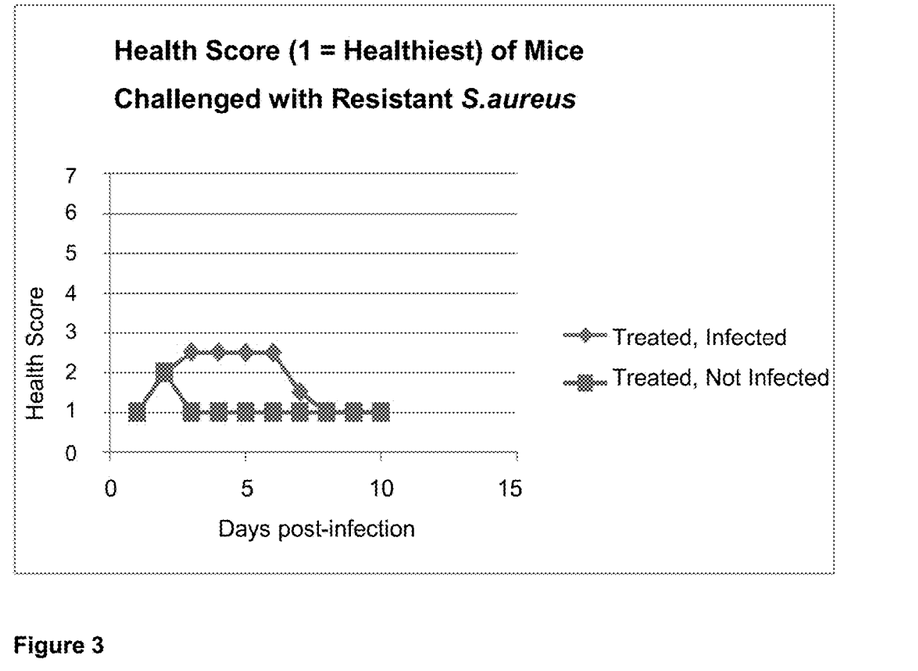
FIG. 3 is a graph of Health Score (See paragraph 176 for an explanation of Health Score) over 10 days, of two groups of 10 mice each, both treated with copolymer MW 500; Example 1 (Ex 1); 132 mg/Kg of mouse; one ("infected") group of mice was infected with *S. aureus* superbug (*S. aureus* USA300) and the second ("not infected") group was not infected with the bacteria. The graph shows the results of Example 7.

Summary.
Route of treatment Tail-injection
Time the treatment was before/after infection: 10 minutes before
Test-treatment by copolymer: Example 1; 132 mg/Kg
Route of infection: Tail-injection Infection by: MRSA (*S. aureus* USA300)
For results, see: FIG. 3.

FIG. 3 demonstrates that at this concentration, firstly the copolymer is not substantially toxic; and secondly the copolymer, in vivo is antimicrobial-active against *S. aureus* superbug.

Example: 8

This example compares the efficacy of the copolymer of Example 1 in accordance with the invention with that of Comparative Example 1 not in accordance with the invention.

Two groups of each 10 mice were infected with *S. aureus* superbug (*S. aureus* USA300), and 24 hours afterwards each group was treated curatively with respectively, copolymer MW 500 Example 1 at 132 mg/Kg of mouse, or copolymer MW 2500 Comparative Example 1 at 167 mg/Kg of mouse. FIG. 4 is a graph of mice having survived after culling due to morbidity or mortality.

Summary
Route of treatment Gavage
Time the treatment was before/after infection: 24 hours after
Test-treatment by copolymer: Example 1; 132 mg/Kg
Comparative-treatment by copolymer: Comparative Example 1; 167 mg/Kg
Negative-control by:
Positive-control by:
Route of infection: Tail-injection Infection by: MRSA (*S. aureus* USA300)
For results, see: FIG. 4.

FIG. 4 shows firstly, that the lower molecular weight copolymer of the invention exhibits higher activity in treatment of parenteral infections in vivo, and secondly, that as a negative control (saline) gave a comparable survival of only 4—the copolymer resists initial metabolism in the liver.

Example: 9

This example compares the survival rate after infection with antibiotic resistant bacteria of subjects treated with copolymers of the invention of Example 1 with copolymers of Comparative Example 1, a positive control (Oxacillin) and negative control (saline).

Figure 5:
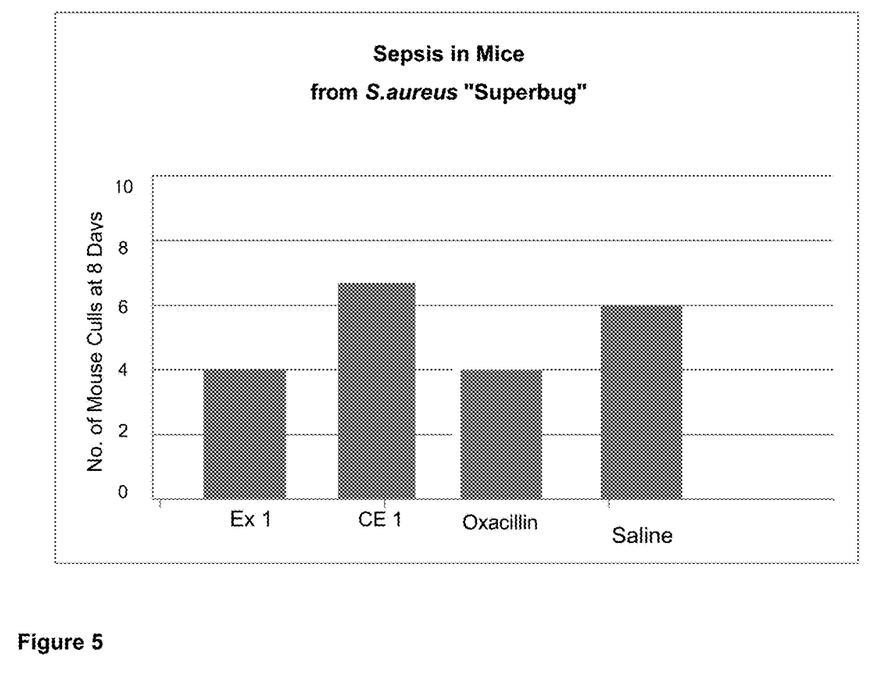
FIG. 5 is a column chart showing the number of mice culled due to morbidity or mortality among four groups of each 10 mice, infected with *S. aureus* superbug (*S. aureus* USA300), and 24 hours afterwards each group treated curatively with respectively, copolymer MW 500 Example 1 (Ex 1) at 132 mg/Kg of mouse, or copolymer MW 2500 Comparative Example 1 (CE 1) at 167 mg/Kg of mouse or positive control Oxacillin, 500 mg/Kg or negative control saline. The experimental procedure is reported in Example 9.

Four groups of each 10 mice were infected with *S. aureus* superbug (*S. aureus* USA300), and 24 hours afterwards each group treated curatively with respectively: The copolymer of Example 1 (Ex 1) MW 500 at 132 mg/Kg of mouse; copolymer MW 2500 Comparative Example 1 (CE 1) at 167 mg/Kg of mouse; positive control Oxacillin, 500 mg/Kg and negative control saline. FIG. 5 is a chart showing the number of mice culled due to morbidity or mortality.

Summary
Route of treatment Tail Injection
Time the treatment was before/after infection: 24 hours after
Test-treatment by copolymer: Example 1; 132 mg/Kg
Comparative-treatment by copolymer: Comparative Example 1; 167 mg/Kg
Positive-control by: Oxacillin; 500 mg/Kg
Negative-control by: Saline
Route of infection: Tail-injection Infection by: MRSA (*S. aureus* USA300)
For results, see: FIG. 5.

It is apparent from FIG. 5 that the lower MW copolymer is more efficacious; It also gave surviving mice having the lowest (healthiest) Health Score=1.0 compared to 3.3. 2.5 and 3.3 respectively, indicating its group had most effectively been restored to good health.

REFERENCES

S. V. Daudouin (2008), "Sepsis", Springer-Verlag
P. J. Flory (1953), "Principles of Polymer Chemistry", Cornell University Press.
G. J. H. Melrose, C. M. Kleppe, J. W. Langley, J. M. Stewart and J. Van Dyk (1988), International Patent Publication WO 88/04671.
G. J. H. Melrose (1996), International Patent Publication WO 96/38186.
G. J. H. Melrose and A. J. Huxham (2000), International Patent Publication WO 00/03723.
G. J. H. Melrose, G. Daly and A. J. Huxham (2001), International Patent Publication WO 01/60874 A1.
G. J. H. Melrose, A. J. Huxham, D. M. G. Tilbrook and V. L. Wycoco (2003), International Patent Publication WO 03/061672 A1.
G. J. H. Melrose (2009), International Patent Publication WO 09/059350.
E. D. Peters (1962) in C. W. Smith, "Acrolein", John Wiley and Sons, Chapter 16, Page 240.
G. Odian (1981), "Principles of Polymerization", John Wiley and Sons, Second Edition.
J. A. Staton and G. J. H. Melrose (2002), International Patent Publication WO 02/26211 A1.
M. Tilbrook (2005), International Patent WO 2005/044874 A1.

The invention claimed is:

1. A method of treating a parenteral bacterial infection in a subject comprising the step of: administering to the subject a copolymer comprising an acrolein derived segment and a polyalkylene glycol oligomer segment, the copolymer having a molecular weight of no more than 1000 Daltons.

2. The method according to claim 1 wherein the acrolein derived segment is a polyacrolein oligomer comprising two or more acrolein residues.

3. The method according to claim 1, wherein the copolymer has a molecular weight of from 400 to 1000 Daltons.

4. The method according to claim 1, wherein the polyalkylene glycol oligomer segment has a molecular weight in the range of from 200 to 600 Daltons.

5. The method according to claim 1, wherein the polyalkylene glycol is polyethylene glycol.

6. The method according to claim 1, wherein the parenteral bacterial infection is selected from the group consisting of: infections of the blood (bacteremia), meninges, lungs, urinary tract, sinuses, skin, wounds, abscesses and surgical procedures.

7. A method according to claim 1, wherein the parenteral infection is an antibiotic-resistant infection.

8. The method according to claim 1, wherein the parenteral bacterial infection is selected from sepsis and bacteremia.

9. The method according to claim 1, wherein the copolymer is administered locally to an infected inter-cellular and/or intra-cellular component, tissue or organ underneath the outer-protective membranes or the skin such as punctures, injections, bites, cuts, wounds, surgery, splits between skin and mucous membranes tissue or organ in an amount effective to provide local treatment of the infected tissue or organ.

10. The method according to claim 1, wherein the copolymer is administered by a route selected from the group consist of: oral administration, inhalation, transdermal delivery and injection.

11. The method according to claim 1, wherein the copolymer is administered by oral administration.

12. The method according to claim 1, wherein the copolymer is administered as an aqueous solution comprising in the range of from 0.01% by weight to 20% by weight of the of the composition.

13. The method according to claim 1, wherein the copolymer is administered orally in the form of a tablet, caplet, syrup or liquid.

14. The method according to claim 1, wherein the copolymer is administered systemically at a dose in the range of from 1 mg to 1000 mg per kilogram of bodyweight per day.

15. The method according to claim 1, wherein the infection is a bacterial infection selected from the group consisting of *Proteus* spp, *Serratia* spp, *Pseudomonas aeruginosa, Neisseria meningitidis, Escherichia coli, Klebsiella pneumoniae, Staphylococcus aureus*, coagulase-negative *Staphylococcus* spp, *Streptococcus pyogenes, Streptococcus pneumoniae, Enterococcus* spp.

16. A copolymer effective in the treatment of parenteral bacterial infection in a subject comprising a acrolein derived segment and a polyalkylene glycol oligomer segment, the copolymer having a molecular weight of no more than 1000 Daltons.

17. The copolymer according to claim 16 wherein the acrolein derived segment is a polyacrolein oligomer.

18. The copolymer according to claim 16, wherein the copolymer has a molecular weight of from 400 to 1000 Daltons.

19. The copolymer according to claim 16, wherein the polyalkylene glycol oligomer segment has a molecular weight in the range of from 200 to 600 Daltons.

20. The copolymer according to claim 16, wherein the polyalkylene glycol is polyethylene glycol.

21. The copolymer according to claim 16, formed by polymerizing acrolein under conditions of alkaline catalysis at a pH no more than 12.0 in an aqueous solution comprising at least 20% w/w water and polyalkylene glycol oligomer in a weight ratio of polyalkylene glycol/acrolein of at least 4.

22. A process of preparing a copolymer comprising an acrolein derived segment and polyalkylene glycol oligomer and having molecular weight of no more than 1000, comprising the step of: polymerizing acrolein under conditions of alkaline catalysis at a pH no more than 12 in an aqueous solution comprising at least 20% w/w water and polyalkylene glycol oligomer in a weight ratio of polyalkylene glycol/acrolein of at least 4 to provide said copolymer.

23. The method according to claim 1, wherein the copolymer is administered by intravenous therapy.

* * * * *